United States Patent
Steen et al.

(10) Patent No.: US 11,326,191 B2
(45) Date of Patent: May 10, 2022

(54) PROCESS FOR PURIFICATION OF MALONIC ACID FROM FERMENTATION BROTH

(71) Applicant: LYGOS, INC., Berkeley, CA (US)

(72) Inventors: Eric Steen, Berkeley, CA (US); Jeffrey Dietrich, Berkeley, CA (US); Johan Van Walsem, Berkeley, CA (US)

(73) Assignee: Lygos, Inc., Berkeley, CA (US)

( * ) Notice: Subject to any disclaimer, the term of this patent is extended or adjusted under 35 U.S.C. 154(b) by 223 days.

(21) Appl. No.: 16/349,948

(22) PCT Filed: Nov. 14, 2017

(86) PCT No.: PCT/US2017/061453
§ 371 (c)(1),
(2) Date: May 14, 2019

(87) PCT Pub. No.: WO2018/089971
PCT Pub. Date: May 17, 2018

(65) Prior Publication Data
US 2019/0284585 A1 Sep. 19, 2019

Related U.S. Application Data

(60) Provisional application No. 62/548,553, filed on Aug. 22, 2017, provisional application No. 62/421,663, filed on Nov. 14, 2016.

(51) Int. Cl.
| | | |
|---|---|---|
| *C12P 7/46* | (2006.01) | |
| *C07B 63/02* | (2006.01) | |
| *C12N 1/02* | (2006.01) | |
| *C12N 1/16* | (2006.01) | |
| *C12R 1/84* | (2006.01) | |

(52) U.S. Cl.
CPC ............... *C12P 7/46* (2013.01); *C07B 63/02* (2013.01); *C12N 1/02* (2013.01); *C12N 1/16* (2013.01); *C07B 2200/13* (2013.01); *C12N 1/165* (2021.05); *C12R 2001/84* (2021.05)

(58) Field of Classification Search
CPC ............. C12P 7/46; C07C 51/00; C07C 51/42
See application file for complete search history.

(56) References Cited

U.S. PATENT DOCUMENTS

| | | |
|---|---|---|
| 2,373,011 A | 4/1945 | Britton et al. |
| 3,360,554 A | 12/1967 | Sotoo et al. |
| 5,168,055 A | 12/1992 | Datta et al. |
| 2003/0004375 A1 | 1/2003 | Mizrahi et al. |
| 2014/0322777 A1 | 10/2014 | Clark et al. |
| 2015/0321990 A1 | 11/2015 | Stensrud et al. |
| 2016/0177345 A1 | 6/2016 | Dietrich et al. |
| 2016/0201151 A1 | 7/2016 | Medoff et al. |
| 2016/0207868 A1 | 7/2016 | Kawamura et al. |

FOREIGN PATENT DOCUMENTS

| | | | | |
|---|---|---|---|---|
| CN | 111620774 | * | 4/2020 | ............. C07C 51/02 |

OTHER PUBLICATIONS

"Hydrocyclone Frequently Asked Questions", https://hydrocyclone.com/faq.htm, Chemindustrial Systems, Inc., Mar. 3, 2004, pp. 1-3.
"Recrystallization Technique Proper Purification of Crystalline Solids" www.rhodium.ws (https://erowid.org/archive/rhodium/chemistry/equipment/recrystallization.html. Jun. 6, 2007, p. 1-3.
International Search Report and Written Opinion issued for PCT/US17/61453 dated Feb. 1, 2018, 9 pages.

* cited by examiner

*Primary Examiner* — Thane Underdahl
(74) *Attorney, Agent, or Firm* — Faegre Drinker Biddler & Reath LLP

(57) ABSTRACT

A process for the preparation of bio-based malonic acid and crystalline calcium malonate is provided. The calcium malonate is highly pure and provides a source of malonic acid made from a renewable carbon source rather than existing processes which rely on the use of petroleum-based products. The calcium malonate provides an improved source of malonic acid, which is important to many industrial processes.

17 Claims, No Drawings

PROCESS FOR PURIFICATION OF MALONIC ACID FROM FERMENTATION BROTH

CROSS-REFERENCE TO RELATED APPLICATIONS

This application claims priority to U.S. Provisional Patent Application No. 62/241,633, filed on Nov. 14, 2016, and to U.S. Provisional Patent Application No. 62/548,553, filed on Aug. 22, 2017. These applications are incorporated herein by reference in their entirety for all purposes.

GOVERNMENT INTEREST

This invention was made with government support under award number 2014-02634-22195 awarded by the United States Department of Agriculture and award number CRD-16-612 awarded by the United States Department of Energy. The government has certain rights in the invention.

FIELD

Embodiments herein relate to compositions derived from and methods for extracting and purifying bio-based malonic acid compositions. In certain embodiments, methods disclosed herein concern fermenting a microorganism capable of producing malonic acid in the presence of a fermentable carbon source and an alkaline earth metal base and optionally also with seed crystals, under suitable fermentation conditions to obtain a fermentation broth that includes an insoluble alkaline earth metal malonate salt. In certain embodiments, the method includes extracting the resulting insoluble alkaline earth metal malonate salt from the fermentation broth, such that the isolated alkaline earth metal malonate salt is substantially free of cells, converting the isolated alkaline earth metal malonate salt to soluble malonic acid, and crystallizing the resulting soluble malonic acid. Other embodiments include a bio-based malonic acid composition. Still other embodiments relate to a method for purifying bio-based calcium malonate from microorganism-containing fermentation broth by separating calcium malonate from the fermentation broth by filtration, followed by the generation of dissolved malonic acid and calcium sulfate crystals in a gypsum reactive crystallizer; and finally the method may include recrystallization of the dissolved malonic acid in a malonic acid crystallizer.

BACKGROUND

The long-term economic and environmental concerns associated with the petrochemical industry have provided impetus for increased research, development, and commercialization of processes that derive industrial and consumer chemicals not from petroleum feedstocks but rather from renewable feedstocks. One approach is the development of biorefining processes to convert renewable feedstocks into products that can replace petroleum-derived chemicals. Two common goals in improving a biorefining process include achieving a lower cost of production and reducing carbon dioxide emissions.

One such presently petroleum-derived chemical is malonic acid (propanedioic acid, CAS No. 141-82-2). Propanedioic acid ("malonate", CAS No. 141-82-2) is currently produced from non-renewable, petroleum feedstocks. Mono- or di-esterification of one or both carboxylic acid moieties of malonate with an alcohol (e.g. methanol or ethanol) yields the monoalkyl and dialkyl malonates, respectively. 2,2-dimethyl-1,3-dioxane-4,6-dione ("Meldrum's acid" CAS No. 2033-24-1) is produced from malonate using either acetone in acetic anhydride or isopropenyl acetate in acid. Malonic acid and chemical derivatives of malonic acid (such as, for example, monoalkyl malonate, dialkyl malonate, and 2,2-dimethyl-1,3-dioxane-4,6-dione ("Meldrum's acid")) are used for the production of many industrial and consumer products, including polyesters, protective coatings, solvents, electronic products, flavors, fragrances, pharmaceuticals, surgical adhesives, and food additives.

Chemical synthesis has traditionally been the preferred route for synthesis of malonate and malonate-derived compounds. For example, dialkyl malonates are produced through either a hydrogen cyanide or carbon monoxide process. In the hydrogen cyanide process, sodium cyanide is reacted with sodium chloroacetate at elevated temperatures to produce sodium cyanoacetate, which is subsequently reacted with an alcohol/mineral acid mixture to produce the dialkyl malonate. Strittmatter et al. report yields of 75-85% (see "Malonic acid and Derivatives" in: Ullmann's Encyclopedia of Industrial Chemistry, Wiley-VCH, Weinheim, N.Y. (2002)). In the carbon monoxide process, dialkyl malonates (also referred to herein as diester malonates) are produced through cobalt-catalyzed alkoxycarbonylation of chloroacetates with carbon monoxide in the presence of an alcohol at elevated temperatures and pressures.

The existing, petrochemical-based production routes to the malonate and malonate-derived compounds are low yielding, environmentally damaging, dependent upon non-renewable feedstocks, and require expensive treatment of wastewater and exhaust gas.

Biological systems for producing bio-based malonate via biological fermentation have been recently described (see U.S. patent application Ser. No. 14/386,272, incorporated herein by reference). However, fermentative production of malonate creates new challenges for extracting and purifying the bio-based malonate produced, and for efficiently integrating extraction and purification processes into the overall production flow.

There remains a need, therefore, for improved methods, processes, and materials for extracting and purifying bio-synthetic or bio-based malonate in high yields from biological fermentation and improved methods, processes, and materials for the subsequent preparation of downstream chemicals and products.

SUMMARY

The present invention provides a variety of techniques for the purification of bio-based malonic acid (malonate) in high yields. The purification techniques include methods for making large and substantially pure calcium malonate crystals that can be separated from impurities to a very great degree.

DETAILED DESCRIPTION

In the following sections, various exemplary bio-based compositions and methods for extracting and purifying these bio-based compositions are described in order to detail various embodiments. It is recognized by one skilled in the art that practicing the various embodiments does not require the employment of all or even some of the specific details outlined herein, but rather that concentrations, times and other specific details may be modified through routine experimentation. In some cases, well known methods or components have not been included in the description.

Provided herein are compositions, methods and processes for extracting and purifying bio-based malonic acid compositions. The current disclosure is based on discoveries made by the inventors of individual methods and specific and powerful combinations of methods for extracting and purifying malonic acid compositions from biological systems, namely fermentation broths. These methods include the inclusion of seed crystals in fermentation broth. These methods also include the removal of important impurities which have been discovered to adversely affect the quality of bio-based malonic acid containing compositions.

In addition to the overall benefit of biological methods for production of chemicals from renewable feedstock, the specific advantages of the methods provided herein include the elimination of hazardous raw materials that are used for production of petroleum-derived malonic acid (e.g., cyanide, and chloroacetic acid), and the elimination of contaminants present in petroleum-derived malonic acid that can affect industrially important characteristics of the final product such as odor and color.

In certain embodiments, provided herein are methods for extracting and purifying bio-based malonic acid compositions from fermentation broth. In certain embodiments, provided herein are methods for preparation of compositions comprising malonic acid produced by a microorganism, such as an engineered microorganism, for example, derived from a renewable carbon source.

Definitions

Unless defined otherwise, all technical and scientific terms used herein have the same meaning as is commonly understood by one of ordinary skill in the art to which this disclosure pertains.

The terms "a" and "an" and "the" and similar referents as used herein refer to both the singular and the plural, unless otherwise indicated herein or clearly contradicted by context.

The term "bio-based" as used herein refers to an organic compound that is synthesized from biologically produced organic components by fermenting a microorganism. For example, malonic acid synthesized from glucose (e.g., derived from cornstarch) by a genetically engineered microorganism is bio-based. Bio-based compounds are distinguished from wholly petroleum-derived compounds or those entirely of fossil origin.

The term "fermentation" or "fermenting" as used herein refers to the feeding of a renewable carbon source (e.g., glucose) to a microorganism under conditions that enable the microorganism to consume the carbon source and to produce malonate.

The term "fermentation broth" as used herein refers to a mixture comprising a fermentation medium (liquid; comprising, for example, organic acids, salts, metals, sugars) and biomass (solid; comprising, for example, cells and cell debris).

The terms "including," "includes," "having," "has," "with," or variants thereof are intended to be inclusive in a manner similar to the term "comprising".

Exemplary methods and materials are described below, although methods and materials similar or equivalent to those described herein can also be used in the practice of the present disclosure and will be apparent to those of skill in the art. All publications and other references mentioned herein are incorporated by reference in their entirety. In case of conflict, the present specification, including definitions, will control. The materials, methods, and examples are illustrative only and not intended to be limiting.

Wherever a range of values is recited, that range includes every value falling within the range, as if written out explicitly, and further includes the values bounding the range. Thus, a range of "from X to Y" includes every value falling between X and Y, and includes X and Y.

Methods for Purifying Bio-Based Malonic Acid

The general methods described herein relate to the purification of bio-based malonic acid from a fermentation broth of a microorganism that is able to produce malonic acid from a fermentable carbon source. In some embodiments, this method may occur at a commercially viable level.

In some embodiments of preparing bio-based compositions from fermentation, a growth vessel, typically a fermenter, can be used to grow a microbial culture that is subsequently used for the production of calcium malonate and/or malonic acid-containing fermentation broth. Such fermentation vessels are known in the art. The general fermentation process can utilize any number of commercially available carbohydrate substrates, preferably glucose. Fermentation methodology is well-known in the art, and can be carried out in a batch-wise, continuous or semi-continuous manner.

In some embodiments, the microbial culture (i.e., fermentation broth) may include a fermentable carbon source (e.g., glucose monohydrate), and, optionally, a source of nitrogen, phosphorous, and additional media components such as vitamins, salts, and other materials that can improve cellular growth and/or product formation, and water. These components may be fed into a fermenter to regulate or promote growth and sustenance of the microbial culture. In some embodiments, the microbial culture may be grown under aerobic conditions provided by sparging an oxygen containing gas (e.g., air or the like). In some embodiments, calcium hydroxide can be provided for pH control during the growth of the microbial culture.

In some embodiments, the microbial culture may include microorganisms capable of producing malonic acid from fermentable carbon sources (e.g., glucose, sucrose, and/or other carbohydrate sugars). Representative examples of microorganisms include, but are not limited to, those selected from the group consisting of *Pichia kudriavzevii* (*P. kudriavzevii*), *Saccharomyces cerevisiae*, *Escherichia coli*, etc., mixtures thereof and the like. A preferred microorganism is a *Pichia kudriavzevii* strain.

In some embodiments, the method may include the following steps: (1) fermenting a microorganism capable of producing malonic acid in the presence of a fermentable carbon source and an alkaline earth metal base under suitable fermentation conditions to obtain a fermentation broth that includes an insoluble alkaline earth metal malonate salt; (2) separating the insoluble alkaline earth metal malonate salt from the fermentation broth such that the isolated alkaline earth metal malonate salt is substantially free of cells; and (3) converting the isolated alkaline earth metal malonate salt to soluble malonic acid; and crystallizing said soluble malonic acid.

In some embodiments, the method may further include the step of (4) removing impurities from the soluble malonic acid prior to crystallizing the malonic acid.

In some embodiments, the method may include growing a microorganism in broth containing fermentable carbon sources (e.g., glucose, sucrose, and/or other carbohydrate sugars, often glucose is the primary carbon source) to produce malonic acid, separation of calcium malonate from the cells and fermentation broth, reactive crystallization of calcium malonate and sulfuric acid in a gypsum crystallizer, and final crystallization in a malonic acid crystallizer.

In some embodiments, the method may further include the step of removing impurities from the soluble malonic acid prior to crystallization of the malonic acid.

In some embodiments in which the alkaline earth metal base is a calcium base, the calcium base may be calcium hydroxide, calcium carbonate, or calcium oxide. In specific embodiments, the alkaline earth metal base is calcium hydroxide. In other embodiments, the alkaline earth metal base is calcium carbonate. In still further embodiments, the alkaline earth metal base is calcium oxide. In those embodiments in which the alkaline earth metal base is calcium hydroxide or calcium carbonate, the insoluble alkaline earth metal malonate salt is calcium malonate dihydrate.

Certain embodiments of the present disclosure relate to malonic acid compositions that are 100% bio-based as determined by ASTM International Radioisotope Method D 6866. Additional embodiments relate to malonic acid compositions that are 100% bio-based and have decreased acetic acid content. By providing increased bio-based content and lower acetic acid content, the composition is more advantageous of use in industry.

In other embodiments of the present disclosure, the method may include a process for purifying calcium malonate from cell-containing fermentation broth, said process comprising the steps of: (1) separating calcium malonate crystals of at least 10 microns in diameter from cell-containing fermentation broth by centrifugation, (2) generation of dissolved malonic acid and calcium sulfate crystals in a gypsum reactive crystallizer, and (3) recrystallization of the dissolved malonic acid in a malonic acid crystallizer. A particularly useful method for separation of the calcium malonate crystals from cell-containing fermentation broth is separation via the use of a hydrocyclone.

In some embodiments, the microorganism is *Pichia kudriavzevii*. In some embodiments, the fermentation of *Pichia kudriavzevii* is carried out in the presence of calcium hydroxide. In some embodiments, the calcium hydroxide is concentrated to 3M.

In other embodiments, the resulting composition is bio-based calcium malonate. In other embodiments, the resulting composition is bio-based malonic acid.

Calcium Malonate Crystals

There are many objectives of the methods disclosed herein. One objective of the methods disclosed herein is to crystallize calcium malonate in well-defined crystals, avoiding the formation of poorly defined calcium malonate crystals of relatively small size, thus permitting easy separation of calcium malonate from calcium malonate-containing fermentation broth. A second objective is to obtain calcium malonate crystals of relatively high purity, free from accompanying cells, organic acids, salts, metals, and residual sugars that are normally contained in the fermentation broth. A third objective is to obtain calcium malonate crystals that can be separated from the fermentation broth with a good yield and at low cost.

Poor calcium malonate crystal quality and size means crystals of a needle-like, spindle-like, or plate-like shape of less than 10 micrometers or an amorphous calcium malonate precipitate. When calcium malonate crystals of poor quality are formed, it is difficult to separate the calcium malonate crystals from the cells and fermentation broth.

Accordingly, as detailed herein, the inventors discovered that large calcium malonate crystals, which are more readily separated from the cells and fermentation broth, can be produced through the introduction of seed crystals to the fermentation. The seed crystals may be any crystal that causes the accumulated calcium malonate in the fermentation broth to crystallize into large crystals. Preferably the seed crystals are calcium malonate seed crystals. National Center for Biotechnology Information. PubChem Compound Database; CID=517114, https://pubchem.ncbi.nlm.nih.gov/compound/417113 (accessed Sep. 10, 2016) and Varughese, P. A., Saban, K. V., George, J. et al. Journal of Materials Science (2004) 39: 6235.

The timing of addition of the calcium malonate seed crystals may be important for obtaining large calcium malonate crystals that can be readily separated from the cells and fermentation broth. In some embodiments, seed crystals can be added at the start of the fermentation (i.e., before the cells begin producing malonic acid) or at any point during the fermentation. In some embodiments, seed crystals can be added once during the fermentation or more than one time during the fermentation. In a preferred embodiment of the methods as disclosed herein, calcium malonate seed crystals are added only to the fermentation at the start of the fermentation.

The formation of larger crystalline forms of the alkaline earth metal malonate salt can be aided by fermenting the microorganism in the further presence of seed crystals. The seed crystals may be any crystals added in any amount that aid in formation of larger crystalline forms of the malonate salt. In some embodiments in which the alkaline earth metal malonate salt is calcium malonate dihydrate, the seed crystals are calcium malonate dihydrate seed crystals (National Center for Biotechnology Information. PubChem Compound Database; CID=517114, https://pubchem.ncbi.nlm.nih.gov/compound/417113 [accessed Sep. 10, 2016] and Varughese, P. A., Saban, K. V., George, J. et al. Journal of Materials Science (2004) 39: 6235). The seed crystals can be added to the fermentation broth at any one or multiple times, including at the start, during, or at the end of the fermenting.

In some embodiments, seed crystals can be added before the amount of alkaline earth metal malonate salt in the fermentation broth exceeds the solubility limit of the alkaline earth metal malonate salt. In some embodiments, the seed crystals may be added to a concentration that is in excess of the solubility limit of the alkaline earth metal malonate salt. In some embodiments in which the alkaline earth metal malonate salt is CaM, CaM seed crystals may be added to an amount that is in excess of the solubility limit of calcium malonate dihydrate (which is about 6 g/11 at 30° C.). In some such embodiments, CaM seed crystals may be added to a concentration of at least 5 g/l, at least 6 g/l, at least 7 g/l, at least 8 g/l, at least 9 g/l, or at least 10 g/l.

If the amount of the accumulated calcium malonate in the fermentation exceeds the saturation solubility of calcium malonate, or exceeds oversaturation, the calcium malonate spontaneously precipitates. The resulting calcium malonate crystals are small, needle-like and difficult to separate from the biomass and fermentation broth. Calcium malonate is soluble to about 6 g/l at 30° C. in fermentation broth; therefore, it may be desirable to add the seed crystals before the dissolved calcium malonate concentration in the fermentation exceeds 6 g/l.

Method of Fermentation

Embodiments of the methods provided herein may include the step of fermenting a microorganism capable of producing malonic acid in the presence of a fermentable carbon source and an alkaline earth metal base under suitable fermentation conditions to obtain an aqueous fermentation broth that includes an insoluble alkaline earth metal malonate salt (i.e., the salt formed between the alkaline earth metal and malonic acid). In some embodiments, seed crystals can be added at the start of the fermentation (i.e., before the cells begin producing malonic acid) or at any point during the fermentation. The microorganism can be any microorganism capable of producing malonic acid. Non-limiting examples of microorganisms include those selected from the group comprising *Pichia kudriavzevii*, *Saccharomyces cerevisiae*, *Escherichia coli*, and derivatives thereof. In some embodiments, the microorganism is a *Pichia kudriavzevii* strain, http://www.mycobank.org/name/Pichia%20kudriavzevii.

As described herein, fermentation may include the inoculation of a microorganism capable of producing malonic acid in the presence of a fermentable carbon source and an alkaline earth metal base under suitable fermentation conditions into fermentation broth containing a fermentable carbon source. The fermentation conditions may be altered as needed for the organism used. In one example, *Pichia kudriavzevii* is grown in an appropriate medium. In some embodiments, malonate salt seed crystals may be further added to the fermentation broth before, during, or both before and during fermentation. A preferred malonate salt is calcium malonate. The amount of seed crystals added to the fermentation can be an amount needed to obtain a concentration above the solubility limit of calcium malonate, which may be about 6 g/l at pH 5. Thus, the concentration of crystals that may be added is about 6 g/l or more.

Suitable media for fermenting typically depend on the choice of microorganism used. A typical nutrient medium contains a fermentable carbon source, a nitrogen source, a phosphorous source, inorganic salts, and optionally other trace organic nutrients, including vitamins that can improve the health and growth of the microorganism. Either a synthetic or a natural medium can be used so long as the microorganism is capable of growth in the medium.

The fermentable carbon source may be any fermentable carbon source. Non-limiting examples of fermentable carbon sources include glucose, sucrose, maltose, glycerol, ethanol, acetic acid, and mixtures thereof. In one embodiment, the fermentable carbon source is glucose. In another embodiment, the fermentable carbon source is sucrose.

The nitrogen source may be any assimilable nitrogen source. Either synthetic or natural nitrogen sources, or a mixture of synthetic and natural nitrogen sources, may be used. Non-limiting examples of synthetic assimilable nitrogen sources include ammonia, ammonium salts (e.g., ammonium sulfate, ammonium carbonate, and ammonium phosphates), and nitrates. Non-limiting examples of natural nitrogen sources include yeast extract and peptone.

Suitable fermentation conditions are typically dependent on the choice of microorganism used (see, e.g., Krahe, M. 2003. Biochemical Engineering. Ullmann's Encyclopedia of Industrial Chemistry). Fermentation conditions include a suitable growth media, suitable fermentation method, suitable temperature, suitable oxygenation, and suitable pH. Details on exemplary fermentation conditions and media recipes are disclosed in U.S. patent application Ser. No. 14/386,272 and are incorporated herein by reference in its entirety.

Suitable temperatures for fermenting typically depend on the choice of microorganism used. In embodiments in which the microorganism is a yeast, a suitable temperature for fermenting can be from 15° C. to 45° C., to 40° C., to 35° C., or to 30° C.; more preferably from 20° C. to 35° C., or to 30° C.; and most preferably about 30° C.

Another key to isolating a high yield of high quality CaM crystals is the size of the crystals. During fermentation, particle size may be measured by a Coulter counter, such as the Beckmann Multisizer 4e. Ideally, the particles of CaM are at least 10 microns in diameter.

To produce malonic acid, oxygen must be transferred into the fermentation broth; in other words, there must be a positive oxygen transfer rate (OTR). Microbial production of malonic acid results in the concomitant formation of the redox cofactors NADH and/or NADPH, which must be recycled to $NAD^+$ and $NADP^+$, respectively, to maintain the redox balance required for cell health and efficient malonic acid production. Molecular oxygen is typically the electron acceptor used to recycle NAD(P)H back to $NAD(P)^+$ and suitable oxygenation of the fermentation broth is required to efficiently produce malonic acid in a fermentation. Oxygenation of the fermentation broth may be generally achieved by pumping in either atmospheric air (i.e., air that is about 21% molecular oxygen) or oxygen-enriched air. The rate at which oxygen is transferred into the fermentation broth (oxygen transfer rate, or OTR), expressed as $mmol-O_2/l/hr$, describes the oxygenation of the fermentation broth. In many embodiments of the present disclosure, the fermentation OTR is at least 5 mmol/l/h, at least 10 mmol/l/hr, at least 20 mmol/l/hr, at least 30 mmol/l/hr, at least 40 mmol/l/hr, or at least 50 mmol/l/hr.

Fermentations at neutral or near neutral pH values (i.e., from about pH 6 to about pH 8) have an increased risk of contamination by undesired, non-malonic acid producing microbes from the external environment. Therefore, it may be preferable for at least a portion, and often a majority, and sometimes all, of a fermentation to be operated at a pH value less than or equal to pH 7. However, at the same time, a high concentration of malonic acid at a low pH is toxic to most microorganisms and results in decreased growth rate, cell viability, and/or malonic acid production. Thus, a suitable fermentation pH depends on both the choice of the microorganism used (i.e., its ability to grow and produce malonic acid at a lower fermentation pH) and the concentration of fully protonated malonic acid in solution. Generally speaking, to decrease malonic acid-induced toxicity it is often desirable to culture the malonic acid producing microorganism at a pH at least as high as the pKa of the first carboxylic acid of malonic acid, and often times at a pH of at least as high as the pKa of the second carboxylic acid of malonic acid. Doing so minimizes the concentration of fully protonated malonic acid the cells are exposed to and thus minimizes malonic acid-induced toxicity.

In some embodiments, the preferred pH of the fermentation is kept around pH 5.0. Using calcium hydroxide to control the pH is a preferred method. The fermentation process may result in a mixture of cells, solid calcium malonate dihydrate (CaM), and a variety of soluble organic compounds (e.g., calcium acetate and calcium succinate). When carrying out the fermentation at pH 5.0, it is important to monitor the concentration of succinate at 11 g/l or below. If the concentration of succinate is too high, it will form an insoluble calcium salt, which will be difficult to separate from the calcium malonate. Achieving high quality, washed and highly pure CaM crystals is important to be able to ultimately provide bio-based malonic acid in high yield.

Various methods can be used to decrease the concentration of succinate in the fermentation broth, including adjustment of the fermentation oxygen transfer rate and/or modification of the fermentation process such that the majority of succinate produced during the fermentation is reconsumed at the end of the run. In many cases, succinate is produced as a byproduct of native yeast metabolism in response to a redox imbalance, due to, for example, an insufficiently low oxygen transfer rate. In these cases, succinate byproduct formation can be decreased by increasing the fermentation oxygen transfer rate and the succinate concentration can be maintained to less than 11 g/l.

A second method useful for decreasing the concentration of succinate concentration in the fermentation broth is to adjust the fermentation process such that any succinate produced is reconsumed by the engineered microbe. Since succinate is a small-molecule required in nearly all microbe's native metabolism, most microbes, including *P. kudriavzevii* as well as other yeast cells, will reconsume succinate once more preferred carbon sources (for example, glucose) have been depleted from the fermentation broth. The operator can allow the concentration glucose to decrease to about zero g/l and the engineered microbe will begin reconsuming the succinate in the broth. While this method can be employed at any point during a fermentation it is typically used at the end of the fermentation. Additionally, this method is particularly advantageous when producing malonic acid since most microbes (including *P. kudriavzevii* and other yeast) cannot reconsume malonic acid; thus, the amount of malonic acid produced in the fermentation is not decreased when using this approach.

The fermentation pH can be controlled by the addition of various inorganic bases at the beginning and/or throughout the course of the fermentation, and the choice of the fermentation base affects the pKa values for the two carboxylic acid groups. In the presence of a monovalent cation (for example, a sodium cation when sodium hydroxide is used as a base) the two carboxylic acid pKa values are about 2.83 and 5.69. Thus, when sodium hydroxide is used as a base the fermentation pH will often be greater than or equal to pH 5.69.

Surprisingly, as detailed herein, the inventors have discovered that the apparent $pK_a$ of the carboxylic acids shift when using calcium hydroxide as base.

According to this discovery, in the presence of certain alkaline earth metals, the second carboxylic acid pKa value surprisingly decreases. For example, in the presence of calcium, the second carboxylic acid pKa of malonic acid decreases to about 3.15. It is therefore possible to ferment a malonic acid producing microorganism at a lower fermentation pH without observing malonic acid-induced toxicity when neutralizing the broth with a calcium base or other alkaline earth metal bases as compared to bases for which the cation is monovalent. In many embodiments, the fermentation pH is less than or equal to pH 7 for all or part of the fermentation. In some embodiments, the fermentation pH is less than or equal to pH 6 for all or part of the fermentation. In some embodiments, the fermentation pH is less than or equal to pH 5 for all or part of the fermentation.

In addition to neutralizing the malonic acid, alkaline earth metal bases also precipitate out the malonic acid from the culture medium as an insoluble alkaline earth metal malonate salt. Suitable alkaline earth metal bases used to neutralize the malonic acid include calcium bases, magnesium bases, and barium bases. The solubility of the resulting malonate salts that form with calcium, magnesium, and barium have a solubility of less than about 5 g/l at room temperature and pressure, and thus aid in efficient separation of the alkaline earth metal-malonate salt from the fermentation broth.

In some embodiments, specific calcium bases useful in accordance with the methods of the present disclosure include calcium carbonate ($CaCO_3$), calcium oxide (CaO), and calcium hydroxide ($Ca(OH)_2$). Specific magnesium bases useful in accordance with the methods of this disclosure include magnesium carbonate ($MgCO_3$), magnesium oxide (MgO), and magnesium hydroxide ($Mg(OH)_2$). Specific barium bases useful in accordance with the methods of this disclosure include barium carbonate ($BaCO_3$), barium oxide (BaO), and barium hydroxide ($Ba(OH)_2$).

Calcium bases are particularly advantageous for use in controlling the fermentation pH in that they are readily available and inexpensive. Calcium and malonic acid react to form calcium malonate dihydrate (CaM), a low-solubility, dense salt that is readily separated from the fermentation broth and the cells contained in the fermentation broth. In some embodiments in which the alkaline earth metal base is a calcium base, the calcium is added as $Ca(OH)_2$, $CaCO_3$, or CaO. In specific embodiments, the alkaline earth metal base is calcium carbonate. In other embodiments, the alkaline earth metal base is calcium oxide. In still further embodiments, the alkaline earth metal base is calcium hydroxide.

The method of addition of the alkaline earth metal base to the fermentation is also important. In some embodiments, the alkaline earth metal base may be added to the fermentation as a slurry, and in these cases it is important to maximize the concentration of the alkaline earth metal base used in this slurry. Use of a dilute base can result in the addition of excess water to the fermentation and can hinder isolation of the alkaline earth metal malonate salt. In some embodiments, in which the alkaline earth metal base is a calcium base, at least a 1M, at least a 2M, at least a 3M, at least a 4M, or at least a 5M solution of $Ca(OH)_2$, $CaCO_3$, or CaO are used to control the fermentation pH. In other embodiments in which the alkaline earth metal base is a calcium base, the calcium base is added dry (i.e., substantially free of water) to the fermentation.

In some embodiments, to maximize yields of the insoluble alkaline earth metal malonate salt, the molar amount of alkaline earth metal may be at least equivalent to the molar amount of malonic acid produced by the microorganism prior to separation of the insoluble alkaline earth metal malonate salt from the fermentation broth. Therefore, in some embodiments, the molar ratio of alkaline earth metal to malonic acid at any time point during the fermenting may be at least 1:1, at least 1.5:1, or at least 2:1. In many embodiments, the molar ratio of alkaline earth metal to malonic acid prior to separation of the insoluble alkaline earth metal malonate salt from the fermentation broth is at least 1:1. In specific embodiments in which the alkaline earth metal base is calcium hydroxide, the molar ratio of calcium hydroxide to malonic acid is at least 1:1.

The alkaline earth metal base can be added to the fermentation broth at any one or multiple times of the fermenting, including at the start (i.e., before the microorganism begins producing malonic acid), during, or at the end of the fermenting (i.e., prior to separation of insoluble alkaline earth metal malonate salt from the fermentation broth).

In some embodiments, the fermentation broth may include an insoluble alkaline earth metal malonate salt. In other words, all or part of the alkaline earth metal malonate salt may be found in a solid form in the fermentation broth. The alkaline earth metal malonate salt in the fermentation broth precipitates from solution when the concentration of alkaline earth metal malonate salt in the fermentation broth exceeds its solubility limit. A higher concentration of alkaline earth metal malonate salt means a larger fraction of total malonic acid produced will be found as the insoluble alkaline earth metal malonate salt. Obtaining a high concentration of alkaline earth metal malonate salt results in higher yields of bio-based malonic acid produced by the methods provided herein, and reduced percentage loss due to solubilized alkaline earth metal malonate salt. In some such embodiments, the concentration of alkaline earth metal malonate salt in the fermentation broth may be at least 75 g/l, at least 100 g/l, at least 110 g/l, at least 120 g/l, at least 130 g/l, at least 140 g/l, or at least 150 g/l. In those embodiments in which the alkaline earth metal malonate salt is calcium malonate dihydrate (CaM), the concentration calcium malonate dihydrate in the fermentation broth may be at least 75 g/l, at least 100 g/l, at least 110 g/l, at least 120 g/l, at least 130 g/l, at least 140 g/l, or at least 150 g/l.

Embodiments of the fermentation method as disclosed herein are not particularly limited and suitable fermentation methods include batch, fed-batch, and continuous fermentations. However, in order to obtain a larger yield of malonic acid, a fed batch culture where the fermentable carbon source is sequentially added over time may be typically used. In many embodiments of the present disclosure, the fermentation method is a fed-batch fermentation method.

Collection of Fermentation Broth

In some embodiments, when the fermentation has been carried out for the desired amount of time, the fermentation broth may be cleared of cells and cells debris by centrifugation. If desired, the process may be carried out by proceeding directly to filtration. Centrifugation can be carried out in a decanter centrifuge, preferably the horizontal type, or hydrocyclones. Hydrocyclones may be used to separate the CaM from the biomass. Hydrocyclones are quite efficient at removing cellular debris from the fermentation broth, which is critically important to the isolation of highly purified CaM crystals. Hydrocyclones work best if the range of total suspended solids is kept at 5-25%. Higher % TSS may result in the loss of CaM to the overflow. If desired the fermentation broth may be diluted or concentrated to bring the % TSS within the 5-25% range. Reproducibility will be enhanced if the process is generally carried out using the same % TSS each time.

In one embodiment, a series of three hydrocyclones may be used to separate the CaM crystals from the majority of the cells. Efficient cell removal is an essential parameter for producing a CaM cake in the subsequent filtration unit operations where the fermentation medium (containing soluble organic and salt impurities) can be washed away from the CaM crystals.

The hydrocyclone separates materials of different sizes and/or densities using a centrifugal force. The centrifugal force is generated by introduction of the slurry into the cyclone under pressure; larger and/or denser particles are pushed to the outside of the cone while smaller and/or less dense particles are kept closer to the center. The vortex finder draws the majority of the water and fine particles to the overflow while the larger/denser materials are drawn out of the apex.

Depending on the scale of the operation, different routes may be followed to obtain CaM crystals from the fermentation broth. In smaller scale or benchtop operations, the underflows from the hydrocyclones can be taken after centrifugation and sent them to a reslurry tank. Wash water from the process can be used to bring the total suspended solids (% TSS) to a level of 20-25%. The use of wash water may help dilute out the cells and the impurities in the fermentation broth.

In larger operations such as continuous or semi-continuous manufacturing, the wash water may be obtained after horizontal vacuum belt (HVBF) unit operation. In either case, reusing wash water may be beneficial due to the solubility of CaM in water at pH 5 (about 6 g/11 at room temperature); thus, more CaM may be recovered by reusing the wash water.

In some embodiments, the fermentation broth obtained at the end of fermenting may be largely free of other insoluble organic acids other than the alkaline earth metal malonate salt. In some embodiments, the fermentation broth at the end of the fermentation may include a lower amount of succinic acid than the amount of succinic acid that would form an insoluble alkaline earth metal succinate salt. In those embodiments where the alkaline earth metal base is a calcium base, the fermentation broth at the end of the fermentation may include less than 11 g/11 succinic acid.

The ease by which the insoluble alkaline earth metal malonate salt can be separated from the fermentation broth and cells contained in the fermentation broth increases with increasing size of the alkaline earth metal malonate salt crystals formed. Conventional procedures for obtaining alkaline earth metal malonate salt crystals typically yield high fractions of crystalline forms of poor quality and small size (i.e., crystals of a needle-like, spindle-like, or plate-like shape of less than 10 micrometers) or of an amorphous alkaline earth metal malonate salt precipitate.

An objective of the methods provided herein is to obtain malonate salt in crystalline form of high quality (i.e., highly pure and well defined) and large size. Therefore, in some embodiments of the methods provided herein, at the end of the fermenting the fermentation broth may include at least 80%, at least 85%, at least 90%, or at least 95%; from 80% to 100%, to 95%, to 90%, or to 85%; from 85% to 100%, to 95%, or to 90%; from 90% to 100%, or to 95%; or from 95% to 100% by weight of insoluble malonate salt in crystalline form.

In some embodiments, the malonate salt may have a diameter of at least 10 µm, at least 15 µm, at least 20 µm, or at least 25 km; between 10 µm and 30 µm, 25 µm, 20 µm, or 15 am; between 15 micros and 30 µm, 25 µm, or 20 µm; between 20 µm and 30 µm, or 25 µm; or between 25 µm and 30 µm. The size of a crystalline form can be measured using a Coulter counter (e.g., Beckmann Multisizer 4e).

In other embodiments, a suitable size of the crystalline form of malonate salt can be defined by determining the ease with which the crystalline form can be isolated from the fermentation broth or certain components in the fermentation broth. Such defining can be done, for example, by centrifuging aliquots of fermentation broths at low g-force and measuring the yield of large crystalline forms (diameters>10 µm) in the pellet obtained and of fine crystalline forms (diameters<10 µm) in the supernatant or suspended fines obtained, and defining as the suitable size of the crystalline form any size that maximizes the yield of the large crystalline forms.

Isolating Insoluble Alkaline Earth Metal Malonate Salt from the Biomass.

One advantage to forming an insoluble alkaline earth metal malonate salt in a fermentation broth is that the alkaline earth metal malonate salt crystals can be separated from both soluble and insoluble impurities in this fermentation broth. Non-limiting examples of soluble impurities include salts, metabolic byproducts produced by the cell, and unconsumed carbohydrates. The primary insoluble impurity present in fermentation broth is cells (i.e., biomass). Cells are particularly problematic in that their occurrence in downstream purification steps can decrease malonic acid yields and product quality through cell lysis and release of various intracellular compounds (e.g., metabolites, proteins, and cell debris). Therefore, it is preferable to separate the insoluble alkaline earth metal malonate salt from both the fermentation broth and cells present in the fermentation broth.

In many embodiments, a process of isolating an alkaline earth metal malonate salt from a fermentation broth involves separating a heavy phase that is enriched in the alkaline earth metal malonate salt and is substantially free of biomass. As used herein, "substantially free" can mean less than 1% w/w, less than 2% w/w, less than 3% w/w, less than 4% w/w, or less than 5% w/w of cells in the heavy phase. If, for example, the heavy phase has a total mass of 1000 kg and contains 750 kg calcium malonate dihydrate and 20 kg cells, the % w/w of cells in the heavy phase is 2% (i.e., 20 kg-cells/1000 kg total mass).

The insoluble alkaline earth metal malonate salt can be isolated from the fermentation broth and cells based on size or mass or density, or a combination of size, mass, and density so long as the isolated insoluble alkaline earth metal malonate salt is substantially free of cells.

In some embodiments, isolation based on size can be accomplished via filtration using, for example, a filter press, candlestick filter, or other industrially used filtration system with a molecular weight cutoff that retains the insoluble alkaline earth metal malonate salt and allows the fermentation broth and cells to pass through.

In other embodiments, isolation based on size and density can be accomplished via settling or centrifugation, using, for example, a settler, centrifuge, or hydrocyclone. Settling, centrifugation, and hydrocyclones all produce a heavy phase, which may be enriched in insoluble alkaline earth metal malonate salt and may be substantially free of cells, and a light phase, which includes primarily the fermentation broth and contains the majority of the cells. When the alkaline earth metal malonate salt is CaM, isolation by settling and/or centrifugation is a particularly attractive option. Yeast cells, for example, typically have a particle size of between 4-6 microns and a density of around 1.1 g/ml. CaM particles, in contrast, are typically greater than 10 microns and have a density of around 1.55 g/ml. The difference in size and density between CaM particles and cells allows for efficient production of a heavy phase enriched in CaM and substantially free of cells.

When separating two solids by centrifugation, two important parameters are time and g-force. When separating an alkaline earth metal malonate salt from cells, any combination of time and g-force can be applied so long as the resulting heavy phase is both enriched in the alkaline earth metal malonate salt and is substantially free of cells. Suitable times and g-forces can be determined using methods known in the art. In some embodiments in which the alkaline earth metal malonate salt is CaM, the CaM can be separated from the fermentation broth by settling at a g-force of 1 for a period of 30 minutes to 2 hours. In other embodiments, the CaM can be separated from the fermentation broth by centrifugation for a period of time from 0.5-3 minutes and a g-force from 200×-g to 500×-g.

In many embodiments, centrifugation can be performed using a decanter centrifuge. Fermentation material can be fed into the decanter, which is operated at pre-determined parameters that allow for efficient production of heavy phase enriched in solid CaM and substantially free of cells.

In some embodiments, the CaM can be separated from the fermentation broth using a hydrocyclone. The centrifugal force in a hydrocyclone is generated by introduction of a slurry into the cyclone under pressure; larger and/or denser particles are pushed to the outside of the cone while smaller and/or less dense particles are kept closer to the center. The vortex finder draws the majority of the water and fine particles to the overflow while the larger/denser materials are drawn out of the apex. Hydrocyclones work best if the solution to be centrifuged has a TSS in the range of from 5% to 25%, or is concentrated or diluted to such TSS, because a higher TSS may result in loss of malonate dihydrate in crystalline form to overflow. In some embodiments, a series of hydrocyclones (e.g., 2, 3, or more hydrocyclones) can be used. In smaller scale or benchtop operations, underflow (i.e., wash water) from a hydrocyclone in the series can be sent to a reslurry tank and used to dilute the solution to be centrifuged to the optimal TSS prior to the next hydrocyclone.

In larger operations, such as continuous or semi-continuous manufacturing, the wash water can be derived from a horizontal vacuum belt (HVBF) unit operation or rotary drum vacuum filter (RDVF), which can be continuously fed by the hydrocyclone underflow. In either case, reusing wash water comprising soluble malonate salt can increase the yield of malonate salt in crystalline form obtained.

In many embodiments, two or more centrifugation steps are used in series. In many cases it is advantageous to use a combination of CaM separation unit operations in series in order to optimize both CaM yields and/or CaM purity. For example, a high g-force centrifugation step (see Example 4) can be used to provide a heavy phase enriched in insoluble CaM at a high yield (for example, a greater than 90%, greater than 95%, or greater than 98% yield of insoluble CaM). The wet CaM cake can then be resuspended to a total suspended solids concentration (for example, between 5-25% TSS) that provides optimum performance on a second, more selective and lower g-force centrifugation unit operation (for example, a low-speed decanter centrifuge as described in Example 3 or a hydrocyclone). The resulting CaM in the heavy phase from the second, low g-force centrifugation step is thus used to achieve a high purity CaM (for example, greater than 95% w/w, greater than 98% w/w, or greater than 99% w/w) than either centrifugation operation could provide alone. Additionally, the centrate from the second centrifugation step can also be recycled to the high g-force centrifugation step to recover any insoluble CaM while rejecting the majority of the yeast and other impurities in this recycle stream, thereby increasing CaM yield. Lastly, in many embodiments, the wash water used in the described series of centrifugation steps is used in countercurrent flow. Washing in countercurrent both reduces the soluble CaM losses and reduces the amount of fresh water used during processing.

Isolation of Calcium Malonate Crystals

After separation from biomass, the calcium malonate crystal-containing fermentation broth can be then passed through an appropriate filter. A particularly preferred filtration method is to pass the liquid through a horizontal vacuum belt filter (HVBF) or rotary drum filter. In some embodiments, the crystals can be collected on the filter and washed. The importance of the filtering and washing of the crystals is to achieve a clean and uniform cake discharge to take into the next step of the process. The hydrocyclone underflow may be continuously output into the HVBF process. The HVBF is the ideal equipment as it allows for multi-stage washing and variable dewatering times. A preferred washing liquid is water.

In a preferred embodiment, hydrocycloned CaM slurry can be applied to the filter bed at about 50% TSS. The slurry can be allowed to sit on the filter for 30 seconds before a full vacuum of 20 in Hg below atmospheric pressure is applied. The slurry can be placed on a filter such that there is an effective filtration surface area of 49 in². The initial filtered cake can then be rewashed twice with distilled or reverse osmosis water and then finally dewatered.

In some embodiments, the slurry comprising filtered or centrifuged alkaline earth metal malonate salt can be further washed and/or dewatered. In some such embodiments, the slurry can be applied to a filter bed at a TSS of about 50% and such that there is an effective filtration surface area of 49 in². In some embodiments, the slurry can be washed at least once with distilled or reverse osmosis water. In some embodiments, the slurry can be dewatered by applying full vacuum of 20 mmHg below atmospheric pressure. Suitable devices for such washing and/or dewatering can include a HVBF or RDVF.

Acidifying Insoluble Alkaline Earth Metal Malonate Salt

The methods provided herein may further include the step of converting insoluble alkaline earth metal malonate salt to soluble malonic acid. Such conversion may be accomplished by acidifying (i.e., protonating) the malonate in the alkaline earth metal malonate salt. Acidification can be accomplished by reacting an aqueous slurry of the alkaline earth metal malonate salt with a mineral acid. Such acidification can produce malonic acid and a corresponding salt comprising the alkaline earth metal of the alkaline earth metal malonate salt and the anion from the mineral acid.

Calcium malonate must be acidified to form malonic acid as the final product, which is often desired. Reacting calcium malonate with a strong acid in water generates malonic acid and the corresponding calcium salt. When sulfuric acid is used, its conjugate base sulfate reacts with the displaced calcium ion to form the slightly soluble salt calcium sulfate (also known as gypsum, which has a solubility of about 2.4 g/L at room temperature). Sulfuric acid achieves two goals: 1) the protonation of malonate to form malonic acid and 2) the removal of calcium from solution via the generation of gypsum. In a preferred embodiment, calcium malonate can be reslurried at 40% TSS to achieve gypsum formation at 25-30% TSS when acidified with 25% sulfuric acid. Use of a sulfuric acid feed concentration of 25% v/v may minimize diluting the malonic acid concentration in the overflow as well as allowing for fine pH control by adjusting the feed rate. When running at a large scale, the sulfuric acid concentration can be increased with the use of more sophisticated pH controllers are used, thus increasing the ultimate malonic acid concentration.

Large gypsum crystal formation has been found to ease the separation of solids using an overflow continuous stirred tank reactor (CSTR) fitted with baffles and a radial flow impeller. Calcium malonate can be fed into the reactor at a constant rate. The concentration of the slurry can be measured so that when reacted with a fed sulfuric acid solution, the resulting gypsum solution can be a 25-30% TSS. The reaction can be controlled by adjusting the flow rate of sulfuric acid solution to keep the reactor volume constant at pH 1.5. Since the precipitated solids concentration may be high, the preferred method of separation in some embodiments may be filtration using an HVBF where washing and dewatering can be applied to the filter cake to recover any residual liquor. HVBF may be utilized in the filtration of gypsum due to the ability to manipulate the wash and drying times. This is important as gypsum tends to retain liquor if crystallization produces fine crystals. A rotary drum vacuum filter (RDVF) may be used in lieu of HVBF, although HVBF may be preferred due to its ability to provide purer gypsum crystals. In order to promote even larger crystal growth calcium seed crystals may be introduced.

In a preferred embodiment, a continuous draft tube baffled crystallizer can be employed.

In some embodiments, the composition may then be crystallized, preferably in a draft tube baffle crystallizer in a solution of 25% aqueous $H_2SO_4$. A continuous crystallization process may be preferred over a semi-batch crystallizer because the crystals are easier to filter, wash and dewater. It also allows for more precise control of the pH which improves the yield of high quality, large calcium malonate crystals.

In some embodiments, water may be added to the crystallizer to achieve the desired reaction volume, in the preferred embodiment this is 395 ml total volume. In some embodiments, gypsum seed crystals, which can be 6% by mass, may be introduced with the agitator operating at 800 rpm. In some embodiments, the calcium malonate slurry may be stirred in a separate vessel. In some embodiments, the feed tubes may be placed in the reactor next to the baffles on opposite sides of one another and the feed outlets placed just outside the tip of the impeller. In some embodiments, the initial feed rates may be such that the calcium malonate and sulfuric acid are fed at the same molar rate and the sulfuric acid feed rate is adjusted to control the pH at 1.5. In some embodiments, the reaction may be carried out at ambient temperature. In some embodiments, the reaction may be carried out for approximately 9 minutes. If desired, the material may again be washed and filtered, preferably on a horizontal vacuum belt filter or rotary drum.

Non-limiting examples of mineral acids that can be used for the acidification step include sulfuric acid ($H_2SO_4$), hydrochloric acid, phosphoric acid, and nitric acid. In some embodiments, a concentrated acid may be used to limit dilution of the soluble malonic acid with water. In many embodiments, a mineral acid may be used that forms an insoluble salt with the alkaline earth metal that is easy to separate from the soluble malonic acid. In some embodiments, the mineral acid is $H_2SO_4$. In some such embodiments, the $H_2SO_4$ has a concentration of at least 10% v/v in water to minimize dilution of the malonic acid.

In embodiments in which the alkaline earth metal salt is CaM, reaction with $H_2SO_4$ yields malonic acid and calcium sulfate (i.e., gypsum). Gypsum is highly insoluble (solubility at room temperature of less than 2.4 g/l) such that conditions can be readily optimized for high yield formation of gypsum in crystalline form of large size that can be easily separated from soluble malonic acid, for examples, via filtration or centrifugation. The inventors have discovered that such optimized conditions may include a molar ratio of $H_2SO_4$ to CaM of at least 1:1 to maximize protonation of the CaM, a temperature of below the temperature at which malonic acid decarboxylates to form acetic acid (i.e., approximately 80° C.), and a pH of between 0.5 and 3 to prevent formation of malonic acid salts. In some embodiments, the CaM may be reslurried at a total suspended solids concentration (TSS) of 40% to achieve gypsum formation at a TSS of 25-30% when acidified with 25% v/v $H_2SO_4$. In some embodiments, formation of gypsum in crystalline form may be aided by addition of gypsum seed crystals during acidification. Gypsum in crystalline form can be isolated from soluble malonic acid based on size or weight or density via filtration or settling or centrifugation as disclosed herein. In some embodiments, separation of gypsum in crystalline form via filtration can be combined with removal of biomass as disclosed herein.

In some embodiments, a continuous draft tube baffled crystallizer may be employed for acidification and formation of gypsum in crystalline form. Crystalline gypsum may be separated in batch or continuously (e.g., using a continuous crystallizer with continuous output to a centrifuge). A continuous crystallization process is generally preferred over a batch or semi-batch crystallization process because the former simplifies filtration, washing, and dewatering of the crystalline form. It also allows for more precise control of the pH, which improves the yield of high quality, large gypsum crystals. Water may be added to the crystallizer to achieve the desired reaction volume. Further, the alkaline earth metal malonate salt slurry may be stirred in a separate vessel. In some embodiments, the feed tubes may be placed in the reactor next to the baffles and the feed rates may be such that the alkaline earth metal malonate salt and $H_2SO_4$ are fed at the same molar rate and the $H_2SO_4$ feed rate is adjusted to control the pH at 1.5.

In some embodiments, it may be important to perform the acidification reaction using conditions that minimize malonic acid decarboxylation and acetic acid formation. Under acidic conditions, malonic acid begins to rapidly decompose at about 80° C.; therefore, it is preferable to perform the acidification reaction at a temperature of less than 80° C. In some embodiments, the acidification reaction may be performed at a temperature of between 20° C. and 80° C., between 30° C. and 80° C., or between 40° C. and 80° C.

In some embodiments, if desired, the resulting salt (e.g., gypsum) may be washed and filtered, on, for example, a horizontal vacuum belt filter or rotary drum filter to capture additional malonic acid an increase the overall unit operation yield.

Removal of Impurities

In some embodiments of the described process, the major impurity contained in the solution after gypsum precipitation is sulfate resulting from the solubility of gypsum and any excess sulfuric acid which has been added. Sulfate may be removed by using barium carbonate to precipitate sulfate as barium sulfate, which has a solubility of 4 mg/L. Other anion exchange resins may be used but barium carbonate prevents more loss of desired product than other resins.

In some embodiments, the methods provided herein further include the step of removing impurities from the soluble malonic acid. Impurities may react with malonic acid and reduce final yields, or contribute to the bio-based malonic acid being of lower purity and having more limited industrial utility.

In embodiments in which the alkaline earth metal malonate salt is CaM and $H_2SO_4$ is used for acidification, a major impurity may be sulfate derived from solubilized gypsum and excess $H_2SO_4$. Sulfate can be removed via anion exchange resins. Alternatively, sulfate can be removed via addition of $BaCO_3$ to form barium sulfate ($BaSO_4$), conversion of the $BaSO_4$ to crystalline form by methods disclosed herein, and isolation of the $BaSO_4$ in crystalline form by methods disclosed herein. In embodiments in which $BaCO_3$ is used it is often preferable to use an at least 1 M solution to reduce dilution of the malonic acid.

In some embodiments, nanofiltration may be used to separate out certain salts, sugars, color forming bodies, and other organic compounds present in the soluble malonic acid solution prior to crystallizing malonic acid. In nanofiltration, the malonic acid solution resulting from the acidification step described above may be filtered through a membrane having pore sizes ranging from 0.0005 microns to 0.005 microns, equating to a molecular weight cut-off of about 100 Daltons to about 2,000 Daltons. Nanofiltration can be useful for removing divalent and multivalent ions, maltose and other disaccharides (e.g., sucrose), polysaccharides, and other complex molecules with a molecular weight greater than malonic acid.

As with the precipitation of gypsum, barium sulfate crystallization is important in the separation of precipitated solids. In some embodiments, a preferred method is to use an overflow CSTR. It is carried out with a barium carbonate slurry and malonic acid solution as feeds. Depending on the crystal size, the precipitated solids may be filtered or centrifuged. Barium sulfate can be precipitated either in batch with the addition of solid barium carbonate or in a continuous crystallizer. Using a continuous crystallizer allows continuous output to a centrifuge for solids removal. Due to the relatively small concentration of sulfate present originally, a 1 M $BaCO_3$ slurry reduces the dilution of the output material to a minimum as well as to ease the stirring and pumping of the slurry. In some embodiments, a similar crystallizer as that described previously may be preferred for this step as well.

In some embodiments, cation and/or anion exchange chromatography may be used to remove specific salts and charged compounds present in the malonic acid solution.

Non-limiting examples of other impurities present in the malonic acid solution include color bodies, hydrophobic compounds, excess cations, volatile compounds (e.g., odorants), chloride ions, and uncatabolized carbohydrates. Many of these impurities can be removed by filtration, chromatography, steam stripping, and/or a combination of these unit operations.

Crystallizing Malonic Acid

The methods provided herein may further include the step of crystallizing the soluble malonic acid. For such conversion, the soluble malonic acid must reach its solubility limit. This can be accomplished by either concentrating the soluble malonic acid to above its solubility limit or by decreasing the solubility limit of malonic acid.

In some embodiments, soluble malonic acid solution may be concentrated by evaporation at temperatures below the decarboxylation temperature of malonic acid. Accordingly, in some embodiments, evaporation can be carried at temperatures no greater than 80° C. In some such embodiments, evaporation can be carried out at a temperature of 65° C. until a malonic acid concentration of greater than 70% (w/w) is reached, which is near the solubility limit of malonic acid at that temperature. In other embodiments, evaporation can be carried out at lower than atmospheric pressure (using, for example, a wiped film evaporator or falling film evaporator) to increase the rate of evaporation and/or decrease the rate of malonic acid decomposition to acetic acid.

Multiple crystallization schemes may be employed. For example, in some embodiments, multiple cycles of evaporation and cooling crystallization can be used to increase the yield of crystalline malonic acid obtained. The final mother liquor resulting from the last crystallization cycle can be sent through a malonic acid recovery/recycle step. Depending on the desired purity specification, the combined recovery yield can be as high as 99%. Further purification/crystallization schemes may be developed to produce greater purity malonic acid in crystalline form.

In some embodiments, activated carbon may be used to remove trace impurities including color and hydrophobic compounds. Impurities may be present in low concentrations, but because the malonic solution must be concentrated greater than 10 fold to achieve crystallization, the impurities must be removed. In some embodiments, cation exchange resin may be used to remove calcium left over from the gypsum precipitation as well as any other residual cationic species remaining in solution. This allows for the protonation of any deprotonated malonic acid which can decrease solubility, thus father increasing crystallization yields.

Using chromatography columns to elute the input solution through both activated carbon and cation exchange resin has been found to reduce final impurity concentrations further than in batch applications with the same amounts of material. In some embodiments, a flow rate of 3 BV/hour achieves an optimal resistance time for absorption. In some embodiments, the use of 1% granular activated carbon on a malonic acid weight basis has also been shown to sufficiently remove any color impurities that affect the final malonic acid crystal purity.

Evaporation

Evaporation is important to isolate solid malonic acid as the final product. Water must be evaporated to achieve a concentration of 76% wt/wt. For example, the solubility of malonic acid increases as the temperature of the solution is increased. At 65° C., 76% wt/wt is the solubility limit. Evaporation can be carried out under reduced pressure to increase the rate of evaporation and reduce the rate of decomposition of malonic acid. Since malonic acid is prone to decarboxylation at high temperatures, an efficient evaporation method at lower temperatures may be required to reduce the yield loss. A wiped film evaporator or falling film evaporator can be incorporated to efficiently concentrate the solution at a reduced pressure.

Further Crystallization

In some embodiments, once the solution has reached the saturation limit of malonic acid at 65° C., malonic acid can be crystallized in a cooling crystallizer. In some embodiments, a final solution temperature of 20° C. allows for a recovery of greater than 50%. This stage of crystallization produces high grade product. Multiple crystallization schemes may be employed at this point.

In one embodiment, "Scheme 1," the method utilizes three cooling crystallization batches in series with the preceding crystallization liquor being evaporated to its saturation limit and sent to the next crystallizer crystallizer. In this scheme, the resulting combined yield of three cooling crystallizers is 89%. The final liquor can then be sent through a malonic acid recovery/recycle step.

In another embodiment, "Scheme 2," the method incorporates a yield recovering evaporative crystallization following the initial cooling crystallization. Depending on the desired purity specification, the combined recovery yield may be as high as 99%. Further purification/crystallization schemes may be developed to produce greater purity product.

Advantages of the resultant crystals from embodiments of the method as described herein will generally be large and of high quality. They will be also be relatively free of cellular contamination, thus providing a source of malonic acid that can be put to many industrial uses.

Compositions

Further provided herein are bio-based malonic acid compositions. For determination of relative or absolute quantities of malonic acid in any of the compositions described herein, any suitable analytical method may be used. For example, malonic acid components of a composition may be quantified by chromatography such as liquid chromatography (e.g., HPLC). Area per area percent (area %) of elution peaks associated with malonic acid and/or byproducts can be measured and quantified using known techniques, or weight per weight percent (w/w % or wt %) of each malonic acid and/or byproducts in a composition may be determined using known techniques for mass assay following HPLC analysis (e.g., by using a standard malonic acid sample having a purity of greater than 99% (e.g., 99.95% pure) as a reference). Malonic acid having a purity of 99.95% derived synthetically using non-renewable carbon may be purchased from Sigma-Aldrich, St. Louis, Mo. For any of the compositions disclosed herein, quantities of malonic acid given as percentages refer to any of the wt %, area %, or vol %, unless specifically indicated otherwise.

In certain embodiments, provided herein are malonic acid compositions (e.g., malonic acid having a purity of about 90% or greater, e.g., about 90%, 92%, 95%, 99%, or 99.5%, more than 95%, more than 96%, more than 97%, more than 98%, more than 99%, more than 99.95%, or more than 99.99%, or greater based on the total composition, where % refers to weight percent, area percent, or volume percent) produced by crystallization of malonic acid from an aqueous solution of malonic acid.

In some variations, the malonic acid may be produced by engineered microorganisms grown in media containing a renewable carbon source. The malonic acid compositions described herein are differentiated from malonic acid derived from chloroacetic acid and cyanide by the presence of substantially lower amounts of impurities.

Examples

Example 1: Method for Fermentative Production of Bio-Based CaM by Recombinant *P. kudriavzevii*, and Subsequent Purification of Bio-Based Malonic Acid In Example 1, a recombinant *P. kudriavzevii* strain was used to produce CaM according to methods of the present disclosure. A sterile fermentation tank was filled half full with a defined medium of 650 g/L glucose, dipotassium phosphate, urea, trace metals and vitamins. The medium had been previously sterilized via heat or filtration. An inoculum of 1% (v/v) yeast *Pichia kudriavzevii* was added. A 3M slurry of $Ca(OH)_2$ was added as needed to maintain a pH of 5.0 throughout the fermentation. A fixed stir and airflow rate was initiated upon inoculation. Antifoam was added at the time of inoculation as well. An oxygen transfer rate of 50 mmol/L/hr was maintained. The fermentation was allowed to continue for 6 days (144 hours) at 30° C. After the fermentation broth was allowed to cool, it was centrifuged 3 times in a hydrocyclone. The result was a concentrated calcium malonate slurry that was then placed on a horizontal vacuum belt filter and washed with water. The resultant calcium malonate cake was diluted with water and placed in a gypsum reactive crystallizer. Sulfuric acid was added at 25% (v/v). This material was then again placed on a horizontal vacuum belt filter. The resultant gypsum cake was placed in a draft tube baffle crystallizer and barium carbonate was added. After crystallization the material was centrifuged to remove the barium sulfate. The material was polished by running it over an activated carbon cation exchange column. This material was placed under vacuum at 65° C. to remove the water. The crystals were diluted in water and put in a draft tube baffle crystallizer at 18° C. and then the water was removed in a vacuum evaporator at 65° C. This was repeated two more times. The result was a fine white crystalline powder.

Example 2: Method for Fermentative Production of Bio-Based CaM by Recombinant *P. kudriavzevii*, and Subsequent Purification of Bio-Based Malonic Acid In Example 2, a recombinant *P. kudriavzevii* strain was used to produce CaM according to the methods of the present disclosure. A pre-sterilized fermentation tank was charged with 4,000 liters of sterile culture medium comprising glucose, a phosphate source, a nitrogen source, salts, and vitamins in amounts known to practitioners skilled in the art as sufficient for enabling *P. kudriavzevii* growth and malonic acid production. The fermenter was inoculated with recombinant *P. kudriavzevii* strain capable of producing malonic acid to a concentration of 0.26 $OD_{600\ nm}$. In this example, the fermentation involved two phases—an initial batch phase followed by a second fed-batch phase. When the majority of the glucose present in the initial batch phase was completely consumed in the batch phase, the fed-batch phase started and additional growth nutrients were pulsed into the fermentation tank. The culture was maintained at a temperature of 30° C. for the entirety of the run. The aeration rate was adjusted at the start of the fermentation to achieve an OTR of 57 mmol/l/hr; the aeration rate was not adjusted further during the remainder of the run. Fermentation broth pH was maintained at approximately 5.0 by addition of a 3M $Ca(OH)_2$ slurry; the addition of $Ca(OH)_2$ along with the production of malonic acid by *P. kudriavzevii* produced a visible CaM precipitate during the fermentation. The fermentation was complete when the fermentation vessel was completely filled and all glucose fed into the fermentation broth was consumed. At this point, the broth pH was gradually increased to 9.0 over the course of an hour through further addition of 3M $Ca(OH)_2$ slurry; since CaM solubility decreases with increasing pH, the pH increase to 9.0 precipitated additional solid CaM from the fermentation broth.

An approximately 10-ml sample was drawn from the fermenter and sub-aliquoted into 2-ml samples. One of the 2-ml samples was used to determine dry cell weight according to methods known to practitioners skilled in the art, with an extra step of HCl addition to dissolve the solid CaM prior to measuring the dry cell weight. Another 2-ml sample was used to determine the amount of CaM produced—the sample was acidified using HCl to dissolve the solid CaM, centrifuged to pellet the biomass, and then the supernatant was analyzed by HPLC to measure the concentration malonic acid. In this example, the fermentation broth had a total mass of 10,550 kg and contained 1,796 kg CaM (17% w/w) and 156 kg cells (1.48% w/w). This example demonstrated fermentation processes useful for producing an insoluble alkaline earth metal malonate salt, CaM. Additionally, by using a concentrated (3M) alkaline earth metal base, calcium hydroxide, the dilution of CaM in the final fermentation broth was minimized and CaM titers were high, about 170 g/l (equating to 99 g/l malonic acid), and greater than 95% of the total CaM in the fermentation broth was present as a solid, an important feature for increasing overall purification yields.

Example 3: Method for Extraction of Bio-Based CaM from Fermentation Broth Through Centrifugation In Example 3, centrifugation was used to process fermentation containing CaM and cells and produce a heavy phase enriched in CaM and substantially free of cells. The fermentation broth used for this example was produced using the same methods described in Example 2. An Alfa Laval NX416 decanter centrifuge was used for this example. The centrifuge was set to obtain a 300×-g force and the inlet flow rate was adjusted to achieve a 10 second residence time. During processing, additional water was added to the fermenter to aid removal of residual CaM stuck on the fermenter sides. After CaM separation using the decanter centrifuge, the heavy phase was a 1,520 kg wet cake enriched in CaM (1027 kg of solid CaM; equating to 67.2% w/w) and substantially free of cells (30.4 kg of cells; equating to 2% w/w). The centrate, or light phase, had a total mass of 7040 kg and contained about 105 kg of fine CaM crystals (1.5% w/w) and 141 kg (2% w/w) of cells. Thus, the majority (82.3%) of the cells present in the original fermentation broth were found in the centrate, or light phase, following centrifugation. The purity of the solid CaM crystals isolated in the heavy phase was determined by HPLC and shown to have a purity of at least 98.25%. The overall CaM yield obtained for the centrifugation step was about 91%. Therefore, this example demonstrated the use of centrifugation as a means to efficiently separate high purity CaM crystals that are substantially free of cells from fermentation broth.

Example 4: Method for Increasing Bio-Based CaM Purity Through Washing and Centrifugation In Example 4, the CaM cake resulting from centrifugation of fermentation broth as described in Example 3 was resuspended in cold water and centrifuged at a high G-force to increase the CaM purity and decrease the amount of residual cells present. Impurities can affect the quality of the final malonic acid product and it is often useful to wash these impurities from the solid CaM prior to subsequent processing.

In this example, a wet cake enriched in CaM and substantially free of cells was separated from fermentation broth using a decanter centrifuge as described in Example 3. The wet cake had a total mass of 3,944 kg and was washed by addition of 2,424 kg cold water. This mixture was then centrifuged with an Alfa Laval NX416 decanter centrifuge operated at 3,000×-g with a 10 second residence time. The washed CaM from this first wash-decant step was 98.9% pure by HPLC analysis and was substantially free of cells (<1.75% w/w cells). The CaM slurry was then washed a second time by further addition of 3593 kg ice-cold water and centrifuging the mixture using the previously described decanter centrifuge operating conditions. The twice-washed CaM was determined to be 99.8% pure by HPCL and contained less than 1.56% w/w cells; this CaM was saved and used for further downstream processing. Thus, this example demonstrated that repeated washing of the wet CaM cake can be used to increase CaM purity and decrease the amount of residual cells present.

Example 5: Method for Acidification of Bio-Based CaM and Method for Removal of Gypsum Impurities Through Crystallization In Example 5, washed CaM (produced by the aforementioned steps in Examples 1-4) was acidified with a mineral acid, sulfuric acid, to solubilize the malonic acid in solution and simultaneously form an insoluble salt, calcium sulfate. First, a high shear mixer was used to ensure a homogenous CaM particle size distribution in a CaM slurry. Then, 20% (v/v) $H_2SO_4$ was added to the CaM slurry to form soluble malonic acid and insoluble calcium sulfate ($CaSO_4$, or gypsum). The reaction was carried out for one hour in a glass, jacketed stirred tank reactor by metered addition of both CaM and $H_2SO_4$ to the reaction vessel. The reaction temperature was maintained at 50° C. throughout the course of the gypsum crystallization period.

The solid gypsum was removed from the soluble malonic acid by centrifugation using a decanter centrifuge operated at a G-force of 3,000×-g. The centrate had a total mass of 4,969 kg and contained 461 kg malonic acid; no cells were measured in the centrate. The heavy phase was a wet gypsum cake with a total mass of 2005 kg and contained 1103 kg gypsum and about 902 kg water. A gypsum rinsing step followed to help capture the malonic acid present in the wet gypsum cake; 2,707 kg of cold water was added to the gypsum cake and the mixture was recentrifuged as described above and the centrate containing the malonic acid was collected. After the two wash steps, 7,758 kg of centrate containing 524 kg malonic acid was collected; thus, the malonic acid yield for the gypsum crystallization step was about 96%.

Example 6: Method for Removal of Sulfate Impurities During the Bio-Based Malonic Acid Purification Process In Example 6, a barium polishing step was used to remove a trace contaminant, sulfate, from the malonic acid solution resulting from Example 5. Because an excess of $H_2SO_4$ was added during the gypsum crystallization, sulfate ions were present in excess in solution with malonic acid. In this example, barium carbonate ($BaCO_3$), which has a very low solubility (ca. 4 mg/l at 25° C.), was used to remove excess sulfate from the solution in the form of $BaSO_4$. Specifically, 24 kg of $BaCO_3$ was added to the malonic acid solution from Example 5 and stirred at 25° C. for 30 minutes. The insoluble $BaSO_4$ was removed by centrifugation at 8,000×-g using a disc stack centrifuge. In this example, a 103 kg of wet cake containing the solid $BaSO_4$ was removed from the malonic acid solution. The centrate had a total mass of 7655 kg and contained 517 kg of malonic acid; thus, the malonic acid yield for the sulfate removal step was about 99%.

Example 7: Method for Polishing to Remove Trace Cation Contaminants from a Solution Containing Bio-Based Malonic Acid In Example 7, a cation exchange polishing step was used to remove trace cation contaminants from the malonic acid solution resulting from Example 6 and further clarify the malonic acid solution. DOWEX G26(H), a cation exchange resin, was used in this step. 362 l of resin was loaded into a column with a 0.6 μm diameter. In this example, 7,655 kg of malonic acid solution resulting from Example 6 was flowed through the chromatography column at a feed rate of 18 l/min. This step produced 7,655 kg of malonic acid solution containing 517 kg of malonic acid; thus, a near quantitative malonic acid yield was obtained for this cation exchange step.

Example 8: Method for Nanofiltration and Diafiltration Polishing to Remove Trace Contaminants from a Solution Containing Bio-Based Malonic Acid In Example 8, a nanofiltration and diafiltration polishing step was used to remove trace contaminants from the malonic acid solution resulting from Example 7 and further clarify the malonic acid solution. Impurities, including glucose and other carbohydrates, color forming bodies, organic acids, and salts, are concentrated during crystallization as water is evaporated and the malonic acid is concentrated in the solution. These impurities can negatively affect the crystallization yield and/or the purity of the final malonic acid product, and it is important to reduce their occurrence in the malonic acid solution prior to crystallization. In this example, nanofiltration was implemented to remove colored impurities and other organic impurities. A GE Duracid NF8040F35 membrane with a 100-200 Da molecular weight cutoff was used. Nanofiltration was carried out at 50° C. with a feed rate of 265 l/min, a transmembrane pressure of 237.8-374.5 psi, and a minimum flux of 24 $l/m^2/hr$. This nanofiltration step produced a permeate with a total mass of 6,064 kg that contained 413.5 kg of malonic acid. The retentate had a total mass of 1,591 kg and contained 103.5 kg of malonic acid. The nanofiltration permeate had a visual reduction in color from a yellow color in the feed to a clear permeate product.

A diafiltration step was used to recover more of the malonic acid remaining in the nanofiltration permeate. The operating conditions were the same as described for the nanofiltration step. This diafiltration step produced a permeate with a total mass of 1,906 kg and contained 111 kg of malonic acid. The retentate had a total mass of 501 kg and contained 51 kg of malonic acid. The permeates from the nanofiltration and diafiltration steps were pooled and saved for future use. In this example, 90% of malonic acid was recovered due to the combination of both nanofiltration and diafiltration steps.

Example 9: Method for Purifying Pure Bio-Based Malonic Acid Crystals

Example 9 shows the crystallization of the final, purified malonic acid product from a portion of the malonic acid solution resulting from nanofiltration and diafiltration conducted in Example 8. In this example, the dilute malonic acid solution produced after the filtration steps described in the present disclosure was concentrated prior to crystallization. Table 1 shows the solubility of malonic acid in water at various temperatures.

TABLE 1

| Malonic acid solubility in water | |
|---|---|
| Temperature (° C.) | % (w/w) |
| 5 | 53.92 |
| 10 | 55.75 |
| 15 | 57.63 |
| 20 | 59.68 |
| 25 | 61.69 |
| 30 | 63.5 |
| 35 | 65.28 |
| 40 | 67.43 |
| 45 | 68.85 |
| 50 | 70.33 |
| 55 | 72.38 |
| 60 | 74.29 |
| 65 | 75.96 |

Water was evaporated from the dilute malonic acid solution at 50° C. to produce a concentrated, 71% (w/w) malonic acid solution. In order to minimize malonic acid decomposition, evaporation was carried out at reduced pressure and at a temperature of 50° C. In this example, evaporation was carried out at 100 Torr, with a feed rate of 33.33 kg/min, and an evaporation rate of 30.59 kg/min. In total, 8,000 kg of malonic acid solution was fed into the evaporator; 7,343 kg of water was removed to produce a 71% (w/w) malonic acid solution (i.e., 466 kg of malonic acid in a total mass of 657 kg).

After evaporation of water, purified malonic acid was crystallized by cooling crystallization. In this example, the 657 kg of 71% w/w malonic acid at 50° C. was cooled to 20° C. at a rate of 0.5° C. per minute, resulting in production of 168 kg of crystallized malonic acid. About 298 kg of malonic acid remained dissolved in solution after the first crystallization cycle. The remaining malonic acid solution was taken through 5 more cycles of evaporation and crystallization to increase the yield of crystallized malonic acid. Table 2 shows how multiple rounds of evaporation and cooling crystallization were used to increase the yield of final, crystallized malonic acid product.

TABLE 2

Crystallization of malonic acid

| Crystallization Round | Volume (l) | Malonic acid crystals removed from solution (kg) | Malonic acid in solution (kg) | Water removed (kg) |
|---|---|---|---|---|
| 1 | 456.04 | 167.88 | 298.45 | — |
| 2 | 291.87 | 107.44 | 191.01 | 59.73 |
| 3 | 186.8 | 68.76 | 122.24 | 38.23 |
| 4 | 119.55 | 44.01 | 78.24 | 24.47 |
| 5 | 76.51 | 28.16 | 50.07 | 15.66 |
| 6 | 48.97 | 18.03 | 32.05 | 10.02 |

Lastly, to reduce their moisture content, the purified malonic acid crystals were dried. To prevent decarboxylation of malonic acid, a vacuum drying oven was used in this Example. Drying was carried out at 50° C. and 50 Torr for 24 hours. The final moisture content was measured at less than 0.5% w/w. The purity of the final malonic acid crystals was assayed by HPLC and determined to be greater than 99% pure.

Example 10: Determination of pH and Ca:Malonic Acid Molar Ratio Required to Achieve Efficient Malonic Acid Purification In Example 10, the second carboxylic acid pKa for malonic acid was shown to decrease to about 3.15 when a malonic acid solution was titrated with calcium hydroxide. The decrease in the carboxylic acid pKa when using a calcium base for control of fermentation pH allows for fermentations to be run at less than neutral pH values without detrimental effects on cell growth or production from high concentrations of soluble malonic acid and/or calcium malonate. Running fermentations at lower than neutral pH is important for minimizing the risk of other, undesired microbes contaminating the fermentation. This example also demonstrated that the dihydrate salt of calcium malonate was formed following addition of calcium hydroxide to a malonic acid solution.

A mock fermentation broth was generated by dissolving 15 g (0.146 mols) malonic acid into 150 mL of DI water. In a step-wise fashion, calcium hydroxide was added to the solution and the pH and was measured; additionally, the occurrence of any insoluble salts was monitored following each addition (Table 3). After about pH 3, corresponding to about a 0.58:1 molar ratio of calcium to malonic acid, a salt precipitate was observed. After about pH 5.3, corresponding to about a 1:1 molar ratio of calcium to malonic acid, further addition of calcium hydroxide resulted in a marked increase in solution pH to about 8. To confirm these results, additional malonic acid was added to the system to obtain a 1:2 molar ratio of calcium to malonic acid. The pH of the solution dropped to about 2.8, but the precipitate remained undissolved. The precipitate was recovered and air-dried. The molar ratios of water, calcium, and malonic acid were then determined, confirming the salt to be calcium malonate dihydrate.

Thus, surprisingly use of calcium hydroxide (an alkaline earth metal base) resulted in an apparent shift in the pKa of the second malonic acid carboxylic acid to about 3.15, as compared to a pKa of about 5.7 when titrating with NaOH. This had the unexpected result of forming an insoluble calcium malonate salt at pH values where formation of calcium bis(hydrogen malonate) was expected (i.e., a 0.5:1 molar ratio of calcium to malonic acid). Thus, in order to achieve an efficient yield of malonic acid separation from the fermentation broth a molar ratio of calcium to malonic acid of about 1:1 needs to be achieved and the pH needs to be greater than about 3.15.

TABLE 3

Calcium:Malonic Acid and Calcium Malonate Dihydrate Precipitate

| Calcium to malonic acid molar ratio | Solution pH | Calcium malonate dihydrate precipitate observed? |
|---|---|---|
| 0 | 1.8 | No |
| 0.31 | 2.6 | No |
| 0.58 | 3.15 | Yes |
| 0.740 | 3.19 | Yes |
| 0.92 | 3.45 | Yes |
| 1.01 | 5.3 | Yes |
| 1.03 | 8 | Yes |

Example 11: Separation of CaM from Fermentation Broth and Cells by Gravity Settling In Example 11, an alternative method to centrifugation, gravity settling, was used to separate CaM from fermentation broth and the majority of cells. Gravity settling is a useful method to separate out CaM because no specialized equipment is required.

First, 250 mL of well mixed fermentation broth (25° C.) comprising about 20 g/l biomass and 67 g/l CaM was poured into a graduated cylinder with internal diameter of 3.81 cm. Measurements of the height of the wet calcium malonate cake height were taken at regular intervals over a period of 225 minutes as the mixture separated. A large amount of CaM was observed to settle within the first minute, creating a 20 cm high, loosely packed cake. The CaM continued to separate from the broth and cells at a settling rate of 0.08 cm/min. After 150 minutes, the majority of the CaM had fallen to the bottom of the graduated cylinder. No cell layer was observed on top of the CaM and the supernatant was visibly cloudy with biomass, indicating that the majority of the cells remained suspended in the fermentation broth and were not carried through with the separated CaM.

Example 12: Effect of Centrifugal Force on CaM Separation Efficiency from Cells in Fermentation Broth In Example 12, centrifugal force was varied to demonstrate how this centrifuge operating parameter can be varied to achieve efficient separation of CaM from the cells present in the fermentation broth. Centrifugation is advantageous over settling in that the higher g-forces decrease processing times.

A 50 mL sample of fermentation broth containing about 165 g/l CaM and about 15 g/l cells was prepared. The broth was well mixed to ensure that a homogenous mixture of CaM and cells in solution. 50-mL samples were pipetted into 50-mL conical centrifuge tubes and centrifuged at g-forces of 100×-g and 500×-g for 20, 60, and 120 seconds. Following centrifugation, the volume of both the CaM and cell layers were determined based on the volume gradations on the centrifuge tube wall; the cell layer was distinguished from the CaM layer by its darker color. Subsequently, the supernatant was decanted, taking care to not disturb the pellet, and then centrifuged in a separate 50-mL centrifuge tube at a force of 2000×-g for 2 minutes. The volume of the CaM pellet was again measured and used to determine the percentage CaM yield.

For the 100×-g force samples, the CaM pellet volumes were all 18 mL for the 20, 60, and 120 second time periods. The cell pellet volumes were 0 mL (20 s), 0 mL (60 s), and <0.5 mL (120 s). When the supernatants were centrifuged at 2000×-g for 2 minutes, only the supernatant from the sample centrifuged at 100×-g for 20 seconds produced a CaM pellet (1.5 mL), equating to about a 92.5% yield of the solid CaM in this example. No CaM pellets were observed from the other two samples, demonstrating a near quantitative yield of the solid CaM.

For the 500×-g force samples, the calcium malonate dihydrate pellet volumes were all 18 mL for the 20, 60, and 120 second time periods. The cell pellet volumes were <0.1 mL (20 s), 0.5 mL (60 s), and 1 mL (120 s). When the supernatants were centrifuged at 2000×-g for 2 minutes, and no additional CaM was pelleted, indicating a near quantitative yield of the solid CaM was obtained at this g-force for all centrifugation times tested.

This example demonstrated that a near quantitative yield of calcium malonate dihydrate was obtained with minimum carry through of cells by adjusting the centrifugation G-force and time. The application of a G-force of 500×-g or higher resulted in undesirable cell carry through along with the CaM in the pellet.

What is claimed:

1. A process for purifying calcium malonate from cell-containing fermentation broth, said process comprising:
   separating calcium malonate crystals of at least 10 microns in diameter in cell-containing fermentation broth by one or more centrifugation steps;
   generating dissolved malonic acid and calcium sulfate crystals, comprising adding sulfuric acid to the calcium malonate crystals from the fermentation broth; and
   recrystallizing the dissolved malonic acid in a malonic acid crystallizer.

2. The process of claim 1 wherein said process also comprises the introduction of seed crystals.

3. The process of claim 2 wherein said seed crystals are calcium malonate.

4. The process of claim 3 wherein said calcium malonate seed crystals are introduced at a concentration of 6 g/l or higher.

5. The process of claim 4 wherein said calcium malonate seed crystals are introduced at the start of the fermentation.

6. The process of claim 2 wherein the seed crystals are introduced at the start of the fermentation.

7. The process of claim 1 wherein at least one centrifugation step is done using a hydrocyclone apparatus.

8. The process of claim 1 wherein at least one centrifugation step is done using a decanter centrifuge.

9. The process of claim 1 wherein the pH of the fermentation broth is maintained at around 5.0.

10. The process of claim 1 wherein the microorganism fermented is a yeast.

11. The process of claim 10 wherein the yeast is *Saccharomyces cerevisiase* or *Pichia*.

12. The process of claim 11 wherein the yeast is *Pichia kudriazevii*.

13. The process of claim 1 wherein the concentration of succinate in the fermentation broth is kept below 11 g/l.

14. The process of claim 1 wherein the centrifugation is carried out with at least two centrifugation steps.

15. The process of claim 14 wherein the centrifugation steps are comprised of:
   a) using a centrifuge with high g-force;
   b) resuspending the wet cake to a total suspended solids concentration of between 5-25% TSS; and:
   c) subjecting the suspended solids to a lower g-force centrifugation.

16. The process of claim 15 wherein the lower g-force centrifugation is carried out in a hydrocyclone apparatus.

17. A process of purifying calcium malonate from cell-containing fermentation broth, said process comprising:
   fermenting *Pichia kudriazevii* in the presence of calcium malonate seed crystals at a concentration of 6 g/l, wherein the pH of the fermentation medium is maintained at about 5.0 and the concentration of succinate is kept at 11 g/l or less;
   separating calcium malonate crystals of at least 10 microns in diameter from cell-containing fermentation broth by one or more centrifugation steps, with one or more of said centrifugation steps being carried out in a hydrocyclone apparatus or decanter centrifuge;
   generating dissolved malonic acid and calcium sulfate crystals, comprising adding sulfuric acid to the calcium malonate crystals from the fermentation broth; and
   recrystallizing the dissolved malonic acid in a malonic acid crystallizer.

* * * * *